United States Patent [19]

Dessau

[11] Patent Number: 4,851,599
[45] Date of Patent: Jul. 25, 1989

[54] STYRENE PRODUCTION

[75] Inventor: Ralph M. Dessau, Edison, N.J.

[73] Assignee: Mobil Oil Corporation, New York, N.Y.

[21] Appl. No.: 210,962

[22] Filed: Jun. 24, 1988

[51] Int. Cl.$^4$ .................. C07C 15/393; C07C 5/09
[52] U.S. Cl. .................................. 585/407; 585/435
[58] Field of Search .......................... 585/407, 435

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |

FOREIGN PATENT DOCUMENTS

| | | |
|---|---|---|
| 0107389 | 4/1984 | European Pat. Off. . |
| 2033358 | 5/1980 | United Kingdom . |
| 2114150 | 8/1983 | United Kingdom . |

OTHER PUBLICATIONS

G. Wengui et al, "IR Study of Framework Vibrations and Surface Properties of High Silica Zeolites", Zeolites, Elsevir Science, Amsterdam, 1985, p. 279.

Ione, Journal of Molecular Catalysis, 31, pp. 355–370 (1985).

Huagong, vol. 15, No. 7 (1986) (with translation).

*Primary Examiner*—Curtis R. Davis
*Attorney, Agent, or Firm*—Alexander J. McKillop; Charles J. Speciale; Marina V. Schneller

[57] ABSTRACT

Catalysis of the reaction to produce styrene from n-octane in the presence of catalysts comprising a dehydrogenation metal and a microporous crystalline material containing a modifier selected from the group consisting of tin, lead and thallium, is described.

8 Claims, No Drawings

STYRENE PRODUCTION

FIELD OF THE INVENTION

The invention pertains to a catalytic one-step transformation of octane to styrene. The catalytic composition for the transformation comprises in combination a dehydrogenation metal, such as platinum, and a microporous crystalline modifier-containing material.

BACKGROUND OF THE INVENTION

Styrene $C_6H_5CH=CH_2$, is the common name for the simplest and by far the most important member of a series of unsaturated aromatic monomers. Styrene is used extensively for the manufacture of plastics, including crystalline polystyrene, rubber-modified impact polystyrene, acrylonitrile-butadiene-styrene terpolymer (ABS), styrene-acrylonitrile copolyer (SAN) and styrene-butadiene rubber (SBR).

Many different techniques have been investigated for the manufacture of styrene. The following methods have been used or seriously considered for commercial production: (1) dehydrogenation of ethylbenzene; (2) oxidation of ethylbenzene to ethylbenzene hydroperoxide, which reacts with propylene to give a-phenylethanol and propylene oxide, after which the alcohol is dehydrated to styrene; (3) oxidative conversion of ethylbenzene to a-phenylethanol via acetophenone and subsequent dehydration of the alcohol; (4) side-chain chlorination of ethylbenzene followed by dehydrochlorination; (5) side-chain chlorination of ethylbenzene, hydrolysis to the corresponding alcohols, followed by dehydration; and (6) pyrolysis of petroleum and recovery from various petroleum processes. The first two methods are the only commercially utilized routes to styrene: dehydrogenation of ethylbenzene accounts for over 90% of the total world production. Methods 4 and 5, involving chlorine, have generally suffered from the high cost of the raw materials and from the chlorinated contaminants in the monomer. Manufacture of styrene directly from petroleum streams (method 6) is difficult and costly.

The two commercially important routes to styrene are based on ethylbenzene produced by alkylation of benzene with ethylene.

Molecular sieves have been used in production of ethylbenzene which is subsequently dehydrogenated to produce the styrene. An ethylbenzene process was developed during the 1970s and was based on a synthetic zeolite catalyst, ZSM-5, developed by Mobil Oil Corporation. Although a number of zeolitic or molecular-sieve-type catalysts have been suggested for benzene alkylations with ethylene, most were characterized by very rapid build up of coke and, consequently, short-on-stream time. The Mobil catalyst represented a breakthrough in zeolite catalysis in that it combines high catalytic activity with relatively good resistance to coke formation. Total worldwide capacity based on the process was anticipated to be more than $3 \times 10^6$ t/yr by 1985.

Molecular sieves include naturally occurring and synthetic zeolites. Certain of these zeolites have been demonstrated to exhibit catalytic properties for various types of hydrocarbon conversions. Zeolites are ordered porous crystalline aluminosilicates having definite crystalline structure as determined by x-ray diffraction studies. Such zeolites have pores of uniform size which are uniquely determined by unit structure of the crystal. The zeolites are referred to as "molecular sieves" because interconnecting channel systems created by pores of uniform pore size allow a zeolite to selectively absorb molecules of certain dimensions and shapes.

By way of background, one authority has described the zeolites structurally, as "framework" aluminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula

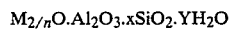

$$M_{2/n}O.Al_2O_3.xSiO_2.YH_2O$$

In the empirical formula, x is equal to or greater than 2, since $AlO_4$ tetrahedra are joined only to $SiO_4$ tetrahedra, and n is the valence of the cation designated m. D. Breck, ZEOLITE MOLECULAR SIEVES, John Wiley & Sons, New York p.5 (1974). In the empirical formula, the ratio of the total of silicon and aluminum atoms to oxygen atoms is 1:2. M was described therein to be sodium, potassium, magnesium, calcium, strontium and/or barium, which complete the electrovalence makeup of the empirical formula. One type of cation may be exchanged entirely or partially with another type of cation utilizing ion exchange techniques in a conventional manner. By means of such cation exchange, it has been possible to vary the properties of a given aluminosilicate by suitable selection of the cation. The cavities and pores are occupied by molecules of water prior to dehydration and/or possibly by organic species from the synthesis mixture in the as-synthesized materials. The prior art describes a variety of synthetic zeolites. These zeolites have come to be designated by letter or other convenient symbols, as illustrated by zeolite A (United States Patent No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702886); zeolite ZSM-11 (U.S. Pat. No. 3,709,979) and zeolite ZSM-23 (U.S. Pat. No. 4,076,842), merely to name a few. The silicon/aluminum atomic ratio of a given zeolite is often variable. For example, zeolite X can be synthesized with silicon/aluminum atomic ratios of from 1 to 1.5, while that ratio in zeolite Y is from 1.5 to 3. In some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as RE. No. 29,948, discloses a porous crystalline silicate made from a reaction mixture containing no deliberately added aluminum and exhibiting the x-ray diffraction pattern characteristic of ZSM-5 zeolites.

SUMMARY OF THE INVENTION

In accordance with the invention, styrene is produced by a catalytic transformation of octane in the presence of a catalyst composition comprising a microporous crystalline material and comprising 0.01 to 20 weight percent, based on the microporous crystalline material, of a modifier selected from the group consisting of tin, thallium and lead and 0.01 to 30 weight percent (based on the weight of said material) of a strong hydrogenation/ dehydrogenation metal. The process is a one-step conversion of normal-octane to styrene.

DETAILED DESCRIPTION OF THE INVENTION

Catalytic conversion of octane to styrene over a catalyst comprising a crystalline microporous material and 0.01 to 20 percent by weight of a modifier selected from the group consisting of tin, thallium and lead and 0.01 to 30 weight percent of metal exhibiting dehydrogenation activity is undertaken at octane dehydrocyclization conditions.

The octane dehydrocyclization conditions include passing n-octane in the vapor state over the catalyst composition described. At atmospheric pressure, temperatures will be greater than about 400° C., preferably above about 500° C. With all other apparent conditions held constant, the selectivity of the reaction to produce styrene appears to vary with temperature.

With all other apparent conditions held constant (including temperature) the selectivity of the reaction to produce styrene may vary with change in partial pressure of normal-octane during contact with the catalyst. It is anticipated that with decreasing partial pressure of normal-octane, under the conditions of the process there will be increase in the selectivity for styrene production.

The catalyst used comprises a hydrogenation/dehydrogenation metal and a non-acidic crystalline microporous modifier containing material preferably a non-acidic crystalline microporous tin containing silicate. As catalysts these compositions can exhibit extremely high selectivity for dehydrocyclization of n-octane to styrene.

The amount of dehydrogenation metal in the catalyst can range from 0.01 to 30 weight percent and preferably 0.01 to 10 weight percent of the non-acidic crystalline microporous indium containing material. In a preferred embodiment, platinum is the hydrogenation/dehydrogenation metal. However, the hydrogenation/dehydrogenation metal can be any Group VIII metal including those of the platinum group, chromium and/or vanadium.

The tin, lead, or thallium modifier content of the crystalline silicates can range from 0.01 to 20 weight percent. Practically, the modifier content will range from 0.1 to 15 weight percent. Preferably the modifier content ranges from about 0.1 to about 10 weight percent.

The crystalline microporous modifier containing material of the invention can contain other elements including boron, iron, chromium and gallium. The content of these other elements in the crystalline containing silicates can range from 0 to 10 weight percent.

The compositions comprising hydrogenation/dehydrogenation metal combined with the crystalline modifier containing silicates do not exhibit any appreciable acid activity. These catalysts would meet the criteria of non-acidic catalysts described by Davis and Venuto, J. CATAL. Vol. 15, p. 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When the crystalline/tin dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

One way of incorporating the modifier into the composition of this invention is by incorporation during the synthesis of the non-acidic crystalline microporous material. Alternatively, the tin, lead, or thallium modifier can be incorporated with the crystalline composition post-synthesis of the microporous crystalline material. The dehydrogenating metal can be incorporated during or after synthesis of the microporous crystalline material. The dehydrogenating metal can be incorporated before, simultaneously with or after modifier incorporation.

Alternatively, reverse procedures can be applied in which the dehydrogenation function is first introduced with subsequent modifier incorporation. Stepwise preparation includes techniques of cocrystallization, impregnation, or exchange. Cocrystallization can be undertaken in a two phase system described in commonly assigned Serial No. 878,555, filed June 26, 1986. Other elements such as boron, iron chromium, gallium, can also be included. Simultaneous incorporation includes the combination of modifier with the dehydrogenation/hydrogenation function during synthesis (i.e., crystallization) or simultaneously after synthesis of the crystalline material.

A modifier free material can be treated with compounds containing modifiers at elevated temperatures. Such treatments can be conducted so that the source of tin is either in the gaseous or the liquid phase including the aqueous phase (such as tin II). Alternatively, a modifier free crystalline reactant can simply be impregnated with a modifier source (e.g., salts of tin, lead or thallium) and then calcined at temperatures above 400° C.

The modifer free reactant can have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

Preferably, the non-acidic crystalline microporous modifier containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous, modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder)

and material of the invention. When used in dehydrogenation and/or dehydrocyclization, the material of the invention will preferably be combined with non-acidic matrix or binder materials. A preferred matrix or binder material would be silica.

EXAMPLES

EXAMPLE 1

Tin ZSM-5 silicate was synthesized in a static system at 300° F. 400 g 28.5% sodium silicate (Q-brand) was added to a solution of 60 g 50% tetramethylammonium chloride, 15 g $SnCl_4.5H_2O$, 30 g 98% $H_2SO_4$, and 60g TPA+Br− in 2250 g water. The mixture was stirred and then placed in a polypropylene bottle in an autoclave for 5 days. The product was 85% crystalline ZSM-5 and consisted of large 5–10 micron crystals. In this and following preparations the zeolitic silicates produced were characterized as having at least one crystal dimension which was at least 0.5 microns; it analyzed for 80.4% $SiO_2$, 0.30% $Al_2O_3$, 3.78% Sn, 2.00% Na, 7.70% C, and 1.05% N.

EXAMPLE 2

Another tin containing ZSM-5 sample was synthesized by dissolving 0.69 g $Sn(II)SO_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

$SiO_2/Sn:H_2O/Sn:OH-/SiO_2: Na+/SiO_2:TPA+/SiO_2$
75:40:0.30:0.35:0.10

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5. SEM indicated an average crystal size greater than 2 microns.

EXAMPLE 3

A tin containing ZSM-5 sample was synthesized in a similar manner except that the $SiO_2/Sn$ ratio was 150 and the $Na+/SiO_2$ was 0.31. The crystalline ZSM-5 product contained 1.36% Sn, 0.0025% Al, 0.93% Na, and 89.31% Ash.

EXAMPLE 4

A tin containing ZSM-5 sample was synthesized in a similar manner except that the $SiO_2/Sn$ ratio was 50, the $Na+/SiO_2$ was 0.38, and the synthesis time was 4 days.

EXAMPLE 5

A tin containing ZSM-5 sample was synthesized at a $SiO_2/Sn$ ratio of 38, a $Na+/SiO_2$ ratio of 0.40, and a synthesis time of 3 days.

Tin incorporation was achieved during the zeolite synthesis, i.e., tin salts were added directly to the high silica ZSM-5 synthesis mixture. SEM data suggests that a significant portion of the tin is located outside of the large crystals formed (FIG. 1). Nevertheless, some tin must be inside the ZSM-5 crystals, since it modifies the selectivity of the platinum, which itself is intracrystalline.

Platinum was incorporated by ion-exchange of the calcined zeolites, probably, via exchange for sodium ions associated with internal silyloxy groups. The presence of intracrystalline (intrazeolitic) platinum was confirmed by the extremely low benzene hydrogenation rates (TON=4 min$^{-1}$ at 100° C.) measured for these catalysts.

EXAMPLE 6

Platinum incorporation into the silicates of Examples 1–5 was undertaken. The as-synthesized tin silicates were calcined first in nitrogen and then in air at 520° C. The calcined materials were ion-exchanged with aqueous $Pt(NH_3)_4Cl_2$ at room temperature; typically, 15–20 mg per gram silicate was used in a non-acidic aqueous medium. The platinum tetramine-containing silicates were then calcined in oxygen to 350° C. at 0.5 C/min.

Elemental analysis of the tin silicate of Example 3 after platinum incorporation indicated Pt=0.80%, Sn=1.54%, Al=31ppm.

Elemental analysis of the tin silicate of Example 1 after platinum incorporation, Pt=0.65%, Sn=3.50%, Al=0.093%.

EXAMPLE 7

Thallium ZSM-5 silicate synthesis was undertaken as follows: A solution was prepared by dissolving 0.85g $TlNO_3$ in 170.6g di-ionized water and then by adding 2.05g NaOH pellets. After all the base had dissolved, 6.38g tetrapropylammonium bromide (TPABr) was added. The resulting solution was transferred to a 300ml stainless steel autoclave and 16.0g of silica gel (SPEX Ind.) was stirred into the solution. The hydrogel produced can be described by the following mole ratios:

$SiO_2/Tl_2O:H_2O/SiO_2:OH-/SiO_2:Na+/SiO_2:TPA+/SiO_2$
150:40:0.20:0.21:0.10

The hydrogel was heated in the autoclave for 4 days at 160° C., with stirring at 400 rpm. The product was filtered, washed and dried. X-ray diffraction analysis indicated it to be 100% crystalline ZSM-5.

Elemental analysis indicated the presence of 8.26% C, 1.88% H, 0.74% N, 0.34% Na, 4.33% Tl, 80.65% $SiO_2$, and 0.0095% Al in the ZSM-5 product.

EXAMPLE 8

Catalyst preparation was undertaken as follows: The as-synthesized thallium silicate was calcined, first in nitrogen and then in air, at 520° C. The calcined zeolite contained 2.43% Tl, 38 ppm Al, and 43.15% Si.

Platinum was incorporated by ion exchange with $Pt(NH_3)_4Cl_2$ (15 mg/g zeolite) at room temperature. TGA ammonia titration in hydrogen indicated the presence of 0.67% Pt. The platinum-containing zeolite was then calcined in oxygen to 350° C. where it was maintained for one hour at 0.5° C./min.

EXAMPLE 9

The "non-acidic" nature of the catalyst of Example 8 was confirmed by its ability to aromatize n-heptane to toluene in high yield. At 538° C. and 30 torr heptane in nitrogen, toluene was formed in 83–88% selectivity at a conversion of 99+%. Total yield of benzene plus toluene was greater than 90%.

EXAMPLE 10

The above catalyst of Example 8 was used to study the reforming of a hydrotreated Arab light naphtha, b.p. 180°–250° F. The reaction was run at 538° C. at atmospheric pressure at 1.8 WHSV and a $N_2$/HC ratio of 2.2. The results obtained are shown below:

|  | Feed | Product | % Converted |
|---|---|---|---|
| $C_1$–$C_4$ | 0 | 0.4 |  |
| Methylpentanes | 16.5 | 11.6 | 30% |
| n-Hexane | 24.2 | 12.2 | 50% |
| Methylhexanes | 15.6 | 11.8 | 24% |
| n-Heptane | 17.1 | 7.2 | 58% |
| Benzene | 2.1 | 14.0 |  |
| Toluene | 3.2 | 11.5 |  |

Preliminary screening of the thallium-modified non-acidic Pt/ZSM-5 catalyst described above for the reforming of a hydrotreated Arab light naphtha, b.p. 180°–250° F., indicated highly selective aromatics formation together with very low $C_1$–$C_4$ gas production. At 538° C., atmospheric pressure, 1.8 WHSV, and a $N_2$:HC ratio of 2.2, preferential conversion of the normal paraffins to benzene and toluene was observed, as shown above.

EXAMPLE 11

Lead-containing ZSM-5 was synthesized. A solution A was prepared by dissolving 3.31g $Pb(NO_3)_2$ in 338.8g de-ionized water. A solution B was prepared by dissolving 12.4g NaOH in 300g de-ionized water. 23.94g TPA bromide was then dissolved in solution B, which was then poured into solution A. 60.0g silica gel (SPEX Ind.) was placed in a 1-liter stainless steel autoclave. The solution was now transferred to the autoclave, and the mixture was stirred for two minutes before sealing the autoclave. Stirring and heating were begun immediately. The composition of the hydrogel formed is described by the following mole ratios:

$SiO_2$/Pb:$H_2O$/$SiO_2$:$OH^-$/$SiO_2$:$Na^+$/$SiO_2$:$TPA^+$/$SiO_2$
90:40:0.30:0.34:0.10

The zeolite crystallization was carried out at 160° C. with stirring at 400 rpm for 4 days. The product ZSM-5 analyzed for 7.96% C, 0.7% N, 0.97% Na, 4.0% Pb, 86.48% ash, and 235 ppm $Al_2O_3$. Platinum incorporation was similar to that in Example 8.

EXAMPLES 12–19

The preparation of the borosilicate ZSM-5 has been described. High silica:alumina ZSM-5 samples containing the elements: chromium, titanium, scandium, nickel, gold, germanium, and zirconium were synthesized in a manner analogous to that used to prepare Tl-ZSM-5, described above. The synthesis conditions are shown in in Table 1 below:

TABLE 1

Synthesis of Metal-Containing ZSM-5

| Example No. | Metal (M) Salt | Mixture Composition (Mole Ratio) |  |  |  |  | Time Days |
|---|---|---|---|---|---|---|---|
|  |  | $SiO_2$/M | $H_2O$/$SiO_2$ | $OH^-$/$SiO_2$ | $Na^+$/$SiO_2$ | $TPA^+$/$SiO_2$ |  |
| 5 | $Pb(NO_3)_2$ | 90 | 40 | 0.30 | 0.34 | 0.10 | 4 |
| 6 | $CrCl_3.6H_2O$ | 75 | 40 | 0.30 | 0.35 | 0.10 | 3 |
| 7 | $TiCl_4$ | 150 | 40 | 0.30 | 0.33 | 0.10 | 5 |
| 8 | $Sc(NO_3)_3.4H_2O$ | 75 | 40 | 0.20 | 0.21 | 0.10 | 4 |
| 9 | $Ni(NO_3)_3.6H_2O$ | 75 | 40 | 0.30 | 0.27 | 0.10 | 3 |
| 10 | $Au(OH)_3$ | 75 | 40 | 0.30 | 0.35 | 0.10 | 3 |
| 11 | $GeCl_4$ | 75 | 40 | 0.20 | 0.25 | 0.10 | 5 |
| 12 | $Zr(NO_3)_4$ | 75 | 48 | 0.26 | 0.31 | 0.10 | 3 |

(all synthesis used SPEX silica, temp = 160° C.), stirred

The synthesized zeolites all contained less than 0.06% Al and more than 0.4% Na. The final platinum-containing catalysts contained 0.57–0.80% Pt.

EXAMPLE 20

The apparent "alpha activity" of the non-acidic platinum containing zeolites was measured using the standard alpha apparatus in either helium or hydrogen over a period of 1–3 hours. The relative hexane conversion activities of the various Pt/ZSM-5 catalysts are shown in Table 2 below:

TABLE 2

Relative Hexane Conversion Activities for Various Pt/ZSM-5 Catalysts

| Catalyst | % Pt | % M | Activity[a] |
|---|---|---|---|
| hi Si | 0.6 | — | 746 |
| Sn | 1.5 | 2.7 | 1013 |
| In | 0.9 | 2.5 | 320 |
| Tl | 0.7 | 4.5 | 94 |
| Pb | 1.4 | 4.5 | 193 |
| Cr | 0.6 | 0.3 | 605 |
| Ti | 0.8 | 1.0 | 865 |
| Sc | 0.6 | 0.9 | 169 |
| Au | 0.7 | 3.9 | 763 |
| Ni | 0.8 | 1.5 | 968 |
| Ge | 0.9 | 0.4 | 691 |
| Zr | 0.6 | 3.1 | 398 |

[a]"Apparent alpha" at 538° C. in He after 1 hour on stream.

(a) "Apparent alpha" at 538° C. in He after 1 hour on stream.

EXAMPLE 21

The catalysts of Table 2 were used in heptane aromatization reactions which were conducted at 538° C. in a down-flow glass reactor, and the reactor effluents were analyzed directly by on-line gas chromatography. Heptane was introduced into the reactor in a nitrogen stream passing through a vaporizer containing n-heptane at 15°–20° C.

The aromatization reaction of n-heptane at 538° C. and 30 torr in nitrogen was chosen to evaluate and characterize various Pt/ZSM-5 catalysts. In general, Pt/ZSM-5 catalysts fell into three broad classes: (1) acidic, producing low overall yields of aromatics and high yields of $C_3$–$C_4$ hydrocarbons; (2) non-acidic, producing significant amounts of both benzene and toluene together with considerable methane; and (3) non-acidic bimetallic (i.e., metal-modified), characterized by extremely high yields of toluene with low methane formation.

The first class was exemplified by a Pt/H-Ga-ZSM-5 material prepared by ion-exchanging out all sodium ions prior to platinum incorporation. Under the test conditions, $C_5^-$ selectivities, mainly propylene and butenes, were greater than 70% while total aromatic selectivities were less than 20%.

The second class was exemplified by non-acidic Pt/ZSM-5 catalysts prepared from a very high silica/alumina ZSM-5 or from a low aluminum content borsilicate (see Table A).

Aromatic selectivities of the reactions catalyzed by Table 2 compositions and reported in Table A were in the 62-66% range with benzene frequently exceeding the toluene produced. The major $C_5^-$ product formed was methane, which was produced in greater than 30% selectivity at high heptane conversions.

Non-acidic Pt/ZSM-5 catalysts, synthesized in the presence of and containing the following elements: chromium, titanium, scandium, gold, nickel, germanium, or zirconium, also fell into this second category as shown in Table A. Some variations in selectivities were observed (primarily as a function of conversion); however, in no case was the yield of toluene greater than 50-55%. Methane was again the prime light gas produced over these catalysts.

In contrast to these bimetallic catalysts, non-acidic bimetallic Pt/ZSM-5 containing the modifiers: indium, tin, thallium, or lead, exhibited dramatically enhanced toluene selectivities approaching 95% or better (on a mole basis).

The improved aromatization selectivity of these catalysts is due to suppression of hydrogenolysis by platinum, especially methane formation. Reduction in hydrogenolysis selectivity of various metal catalysts by alloying with other metals so as to form more selective mixed metal clusters has been reported in the literature, J. H. Sinfelt, "Bimetallic Catalysts", J. Wiley, New York, 1983; L. Guczi, in Stud. Surf. Sci, Cat., Elsevier, Amsterdam, 1986, vol. 29, p. 547; J. Volter, in Stud. Surf. Sci. Cat., Elsevier, Amsterdam, 1986, vol. 27, p. 337.

What is claimed is:

1. A process for producing styrene from n-octane comprising contacting n-octane over a catalyst composition, under conditions effective to dehydrocyclize n-octane to styrene, wherein the catalyst composition comprises a dehydrogenation/hydrogenation metal, a non-acidic crystalline microporous material containing a modifier wherein the modifier is selected from the group consisting of tin, lead and thallium, and wherein the modifier content of the composition ranges from 0.01 to 20 weight percent; wherein the dehydrogenation/hydrogenation metal comprises 0.01 to 30 weight percent and, by said contacting, producing styrene.

2. The process of claim 1, wherein said material is a silicate.

3. The process of claim 2, wherein the silicate has the X-ray diffraction pattern of ZSM-5.

4. The process of claim 1, wherein said n-octane is admixed with an inert diluent under said conditions of contacting.

5. The process of claim 1, wherein said n-octane is in the vapor state.

6. The process of claim 3, wherein said n-octane is in the vapor state.

7. The process of claim 1, wherein said conditions include a temperature of at least about 400° C.

8. The process of claim 1, wherein said conditions include a temperature of at least about 500° C.

* * * * *